United States Patent [19]
Hill

[11] Patent Number: 5,690,964
[45] Date of Patent: Nov. 25, 1997

[54] NON-TOXIC RODENT DETERRENT

[76] Inventor: Cindy J. Hill, 18511 - 273rd Ave. SE., Monroe, Wash. 98322

[21] Appl. No.: 743,890

[22] Filed: Nov. 6, 1996

Related U.S. Application Data

[60] Provisional application No. 60/007,260 Nov. 6, 1995.
[51] Int. Cl.⁶ .................. A01N 25/08; A01N 25/26; A01N 63/00
[52] U.S. Cl. .................. 424/545; 424/417; 424/421; 424/543; 514/920
[58] Field of Search ................. 424/417, 421, 424/543, 545; 514/920

[56] References Cited

U.S. PATENT DOCUMENTS 4,795,637  1/1989  Harding, Jr. ................ 424/195.1
5,464,625  11/1995 Nolte et al. ................ 424/405

OTHER PUBLICATIONS

Chemical Abstracts 108: 108140 (1988).
Chemical Abstracts 124: 23905 (1995).
Chemical Abstracts 120: 238255 (1994).
Lifesci Abstracts, Accession No. 94: 18348 (1993).

*Primary Examiner*—John Pak
*Attorney, Agent, or Firm*—Rustan J. Hill

[57] ABSTRACT

A non-toxic rodent deterrent made from dried fecal matter and/or dried urine from mammals of the Mustelidae Family (e.g. weasels, ferrets, minks, martens, etc.). The rodent deterrent material may be used in its bulk from or this material may be placed in a container for either interior or exterior use.

10 Claims, 1 Drawing Sheet

NON-TOXIC RODENT DETERRENT

This invention was disclosed in and claims the priority date of Provisional Application number 60/007260, filed on Nov. 6, 1995, entitled NON-TOXIC RODENT DETERRENT now abandoned.

BACKGROUND OF THE INVENTION

1. Field of the Invention

The present invention relates generally to methods of preventing rodent infestation of houses, buildings, or ground areas and, more particularly, to a rodent repellant/deterrent which is non-toxic or non-poisonous, so as to prevent rodent infestation without the risk of children, domestic cats, dogs, livestock, or wild animals being inadvertently poisoned by the handling or consumption of toxic chemicals, and/or dead rodents.

2. General Background

Rodent infestation of homes, outbuildings, and lawn areas is a common problem. The principal culprits are house mice (*Mus musculus*) and rats (*Rattus norvegicus* and *Rattus rattus*).

Typically, rodents are controlled using either traps, domestic cats or poisons. The over 300 patents on mouse traps alone demonstrates the effort to control these rodents. The use of a trap requires that the trap be properly baited and set. If the trap functions properly then the trap must be emptied of a dead or maimed rodent. Furthermore, proper disposal of the animal caught is required.

Domestic cats, if trained to catch and kill mice can also control the mouse or rat population. Cats, however, can be costly since they require proper care (veterinary check-ups and shots) and feeding, if kept as pets. Furthermore, cats will often bring the rodent to their owner to show the owner they are doing a good job. If the rodent is not dead and the cat releases the rodent, there now is a problem of a live rodent deposited or remaining in the residence or building. Sometimes the rodent is consumed, and the cat may acquire stomach or intestinal parasites, which requires additional veterinary care. Cats may also consume only portions of the rodent, leaving unwanted "presents" in the owner's residence, doorstep or building.

Another rodent control method is the placement of poisons or poisoned food for the rodents to eat. This method also has draw-backs, since the mice or rats may consume the poison and die, leaving unwanted dead carcasses in inaccessible locations, such as within walls, ceilings, basements and crawl spaces. The subsequent decay may cause unpleasant odors in the house or building, and attract additional pests. Should a rodent die in an accessible location, however, there is the risk of a child, pet, livestock or wild animal coming into contact with the poisoned rodent and ingesting the poison by handling or consuming the poisoned rodent.

Furthermore, all three of the common approaches to rodent control are only effective after the rats and mice have gained access and entered the house, structure or outbuildings, rather than serving to prevent the initial entry.

Accordingly, there exists a need for a method for deterring mice, rats and other rodents from infesting houses, outbuildings, lawns, gardens or other areas which is non-toxic and harmless to humans, domestic pets, livestock and wild animals, and which does not require the setting of traps or the disposal of dead or injured pest animals.

SUMMARY OF THE INVENTION

The present invention has solved the problems cited above, and comprises broadly a non-toxic rodent deterrent. A mixture of (a) dried fecal matter and/or dried urine from Mustelidae family mammals (e.g. weasels, ferrets, minks, martens, etc.) and (b) sand is used as the deterrent material. For indoor use, there is provided a container which has at least one vent opening. A cotton ball is placed inside the container, between the mixture and the container opening. A screen covers the container opening, and is bonded to the container to prevent removal of the screen. A cap is installed over the container opening; the cap can be either removable or permanently bonded to the container. If the cap is bonded then the cap must provide a resealable means for air and water ingress, and for egress of air carrying the deterrent agents/compounds. For exterior use, bulk deterrent material may be used, or the deterrent may be contained as described above.

DESCRIPTION OF THE PREFERRED EMBODIMENT

Figure 1:
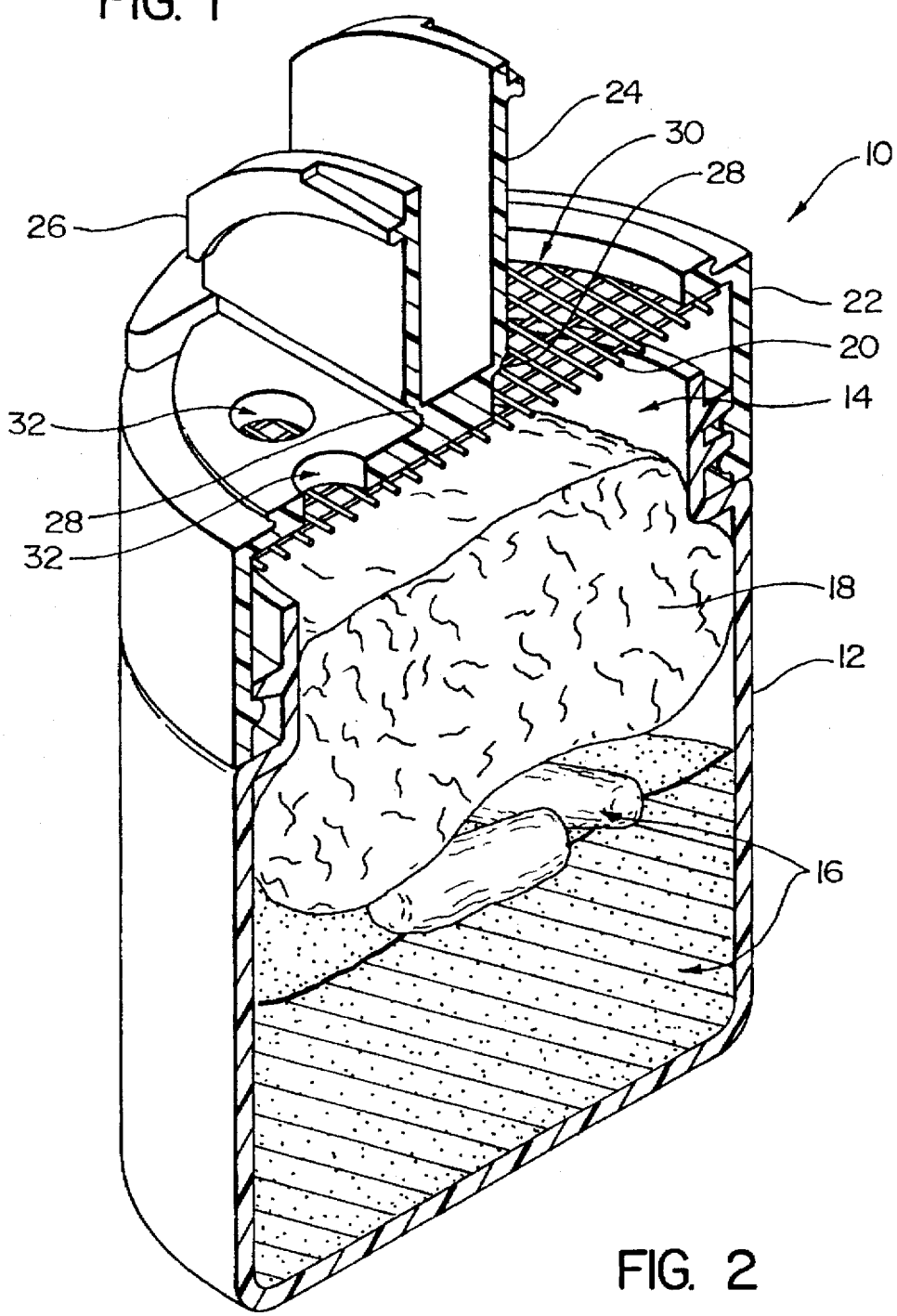
FIG. 1 is a perspective view of a vertical cross-section taken through a non-toxic rodent deterrent assembly in accordance with the present invention, this assembly comprising a container for the deterrent material, cotton and screen for retaining and preventing access to the deterrent material, and a permeable cover allowing ingress of air and water and egress of air.

FIG. 1 illustrates a non-toxic rodent deterrent assembly 10 for either exterior or interior use, in accordance with the present invention. The deterrent assembly 10 includes a container 12 having a single opening 14. Container 12 can be made of any material which will not be significantly damaged by exposure to weather and water for a period of at least one year. Additionally, container 12 can be any size, however, the size of the container 12 will determine the maximum amount of deterrent material 16 residing inside container 12. The preferred container is a one ounce (two liquid ounces) polypropylene jar with a snap-open lid, similar to containers used to dispense household spices.

Inside container 12 resides a suitable quantity of non-toxic rodent deterrent material 16. The quantity of deterrent material 16 used is determined by the size area to be protected. The preferred method of protecting a large area, however, is to employ several small containers in lieu of one large container. Approximately 0.5–1.5 ounces (volume) of deterrent material 16 can protect up to 1500 square feet of floor area for up to one year. Optimal results have been achieved using approximately 1 ounce (volume) of deterrent material 16 to protect 500 square feet of floor area for a period of four to six months.

Deterrent material 16 is prepared by slowly drying feces and urine of ferrets (*Mustela putorius*) or other Mustelidae family mammals at low temperatures. Deterrent material 16 is obtained by collecting feces mixed with sand and urine coated sand from the "litter box" of a Mustelidae family mammal, a collection cycle of about two to four days being suitable. In addition to serving as a substrate for the urine, the sand adds weight which stabilizes the rodent deterrent assembly 10, minimizing the chance that this assembly will be tipped over onto its side. Next the feces and urine coated sand mixture is dried. The most effective proportion of feces to urine appears to be that which is naturally produced by the Mustelidae family mammal, however, the deterrent is still effective as long as there is some small amount of both feces and urine in the deterrent material 16. The preferred method of drying the feces, urine, and sand mixture is to use a dehydrator set on low (80°–100° F.) and to dry the material for about 24 hours. The drying at these temperatures prevents the thermal decomposition of the active deterrent chemicals in the feces and urine. A mixture of fresh feces, and urine would have a similar deterrent effect, but the drying allows for easier packaging, transporting, and extends the shelf life of the deterrent material, since the presence of water accelerates the feces decomposition. In the present invention the dried deterrent material 16 is subsequently activated for use by the addition of an amount of water approximately equal to the volume of the deterrent material 16. To ensure product safety the deterrent mixture 16 should be tested for *E-coli* 0157:H7 bacteria. Additionally, this mixture should be tested for the disease Cryptosporidiosis if young ferrets are used and kept in conditions similar to those experienced by lab ferrets. Furthermore, the health of the animals use to produce the feces should be monitored to minimize the chance of infection or diseases which may be deposited in the feces. Positioned between the deterrent material 16 and the container opening 14 is an absorbent member 18. This absorbent member must be able to absorb water and allow air to circulate through container 12. The preferred material is cotton, however, any other suitable material, such as natural or synthetic sponge, could be used. The container opening 14 is covered by a screen 20. Screen 20 must have holes which are sized sufficiently large to allow air to flow freely through them yet small enough to prevent flies and other small insects from entering container 12. The preferred material for screen 20 is a mesh formed of a tough, durable, synthetic material such as nylon, plastic, or fiberglass with approximately 100 to 150 openings per square inch. The combination of absorbent member 18 and screen 20 prevents either the escape of the deterrent material 16 or access to the deterrent material 16 from outside the container. Screen 20 is permanent bonded to container 12 using any adhesive compatible with the materials selected.

Figure 2:
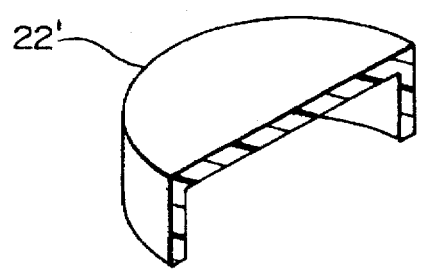
FIG. 2 is a perspective view of a vertical cross-section taken through a simplified cap member for the deterrent assembly which is shown in FIG. 1.

Covering screen 20 so as to seal opening 14 is a cap 22. This cap may be a simple removable cap 22', as shown in FIG. 2, or a cap 22, as shown in FIG. 1, which allows the amount of airflow through the container to be adjusted. The preferred cap 22 is bonded to a container 12 and made from any material compatible with container 12 and screen 20, preferably a non-corrosive material such as polypropylene. Cap 22 has a large flap 24 and a small flap 26. Both flaps seal when shut and are preferably connected to cap 22 by integrally molded hinges 28. In some embodiments, hinges 28 may be dispensed with, however, in such cases it is desirable to have a lanyard or some other means of attaching these flaps to the cap 22 in order to prevent the loss of the former caps. Opening the larger flap 24 provides access to large opening 30; which provides a convenient opening for adding water to activate the deterrent material 16. Additionally, the large opening 30 provides a relatively large initial air flow when first activating the rodent deterrent material. The smaller flap 26, in turn, provides a controlled relatively small air flow through openings 32, which are selected to have sufficient area to provide effective dissemination of the airborne deterrent agents, while preserving the effectiveness of the deterrent assembly for a predetermined period after initial activation.

Rodent deterrent assembly 10 is used by placing this container in the general area where it is desired to deter rodents from entering or remaining. Both the large flap 24 and the small flap 26 are opened (or the simple cap 22' is removed), and a volume of water approximately equal to the volume of deterrent material 16 is added through opening 30. Large flap 24 is closed after about one day to one week, or after the mice have left, while the smaller flap 26 remains open to enable dissemination of a sufficient quantity of deterrent agents by natural air currents to prevent the rodents return. Water may be added as necessary to maintain the deterrent material in a damp condition, by repeating the above procedure, typically being required every three to four weeks. The rodent deterrent assembly 10 should be replaced after 4–6 month of continuous use in order to maintain maximum effective deterrent from entry for most common rodents.

As an alternative to using the non-toxic rodent deterrent assembly described above, the deterrent material 16 may be deployed in bulk form. The bulk use of deterrent material 16 is preferred for use in those areas where aesthetics are of little concern, such as around a residence or building foundation, basement and attic areas, lawns and gardens. When deterrent material 16 is used in bulk, it may either be spread or placed in small piles of 0.5 or 1.5 ounces for each 500 square feet of surface area to protect. If small piles are used, they should be spaced so that there is an overlap in the area to be protected, so as to prevent rodent infestation.

Having then described the present invention in its preferred embodiments, it should be understood that modification and adaptations may be resorted to without departing from the spirit thereof. Accordingly, this invention is not to be limited except as by the appended claims.

What is claimed is:

1. A non-toxic mice and rat (*Rattus norvegicus* and/or *Rattus rattus*) deterrent which comprises:
   a container; and
   an effective amount of deterrent material, said deterrent material residing inside said container, said deterrent material comprising:
      dried fecal matter from a mammal of the Mustelidae Family; and
      substrate coated with dried urine from a mammal of the Mustelidae Family.

2. A non-toxic nice and rat (*Rattus norvegicus* and/or *Rattus rattus*) deterrent of claim 1, wherein said mice is house mice (*Mus musculus*).

3. A non-toxic mice and rat (*Rattus norvegicus* and/or *Rattus rattus*) deterrent of claim 1, wherein said substrate is sand.

4. A non-toxic mice and rat (*Rattus norvegicus* and/or *Rattus rattus*) deterrent of claim 1, wherein said container comprises:
   a container having at least one opening; and
   at least one removable cover for each said at least one opening whereby said container may be opened or closed.

5. A non-toxic mice and rat (*Rattus norvegicus* and/or *Rattus rattus*) deterrent of claim 4, wherein said container further comprises:
   a screen, said screen fixed across said at least one opening; and
   cotton, said cotton residing inside said container between said screen and said rodent deterrent material, wherein said cotton allows air to circulate through said container and absorbs water added to said container, whereby said deterrent material is maintained in a moist and active condition, and air circulating through said container disseminates said deterrent material.

6. A non-toxic mice and rat (*Rattus norvegicus* and/or *Rattus rattus*) deterrent of claim 5, wherein said mice is house mice (*Mus musculus*).

7. A method of manufacturing a non-toxic mice and rat (*Rattus norvegicus* and/or *Rattus rattus*) deterrent comprising:

collecting feces from a mammal of the Mustelidae Family;

collecting urine from said mammal of the Mustelidae Family;

coating a substrate with said urine; and drying said feces and said urine coated substrate.

8. A method of manufacturing a non-toxic mice and rat (*Rattus norvegicus* and/or *Rattus rattus*) deterrent of claim 7, wherein said mice is house mice (*Mus musculus*).

9. A method of manufacturing a non-toxic mice and rat (*Rattus norvegicus* and/or *Rattus rattus*) deterrent of claim 7, further comprising:

placing said dried feces and said dried urine coated substrate in a container.

10. A method of manufacturing a non-toxic mice and rat (*Rattus norvegicus* and/or *Rattus rattus*) deterrent of claim 9, wherein said mice is house mice (*Mus musculus*).

* * * * *